United States Patent [19]

Bernstein

[11] Patent Number: 4,591,555
[45] Date of Patent: * May 27, 1986

[54] MALATE DEHYDROGENASE METHOD

[76] Inventor: Larry H. Bernstein, 1725 Campus Dr., Binghamton, N.Y. 13903

[*] Notice: The portion of the term of this patent subsequent to Sep. 24, 2002 has been disclaimed.

[21] Appl. No.: 488,693

[22] Filed: Apr. 27, 1983

Related U.S. Application Data

[63] Continuation-in-part of Ser. No. 431,028, Sep. 30, 1982, Pat. No. 4,543,327, which is a continuation-in-part of Ser. No. 340,132, Jan. 18, 1982, abandoned, which is a continuation of Ser. No. 158,121, Jun. 10, 1980, Pat. No. 4,311,791.

[51] Int. Cl.$^4$ ............................ C12Q 1/32; C12N 9/99
[52] U.S. Cl. ......................................... 435/26; 435/184
[58] Field of Search ................. 435/26, 291, 805, 810, 435/184

[56] References Cited

U.S. PATENT DOCUMENTS 4,311,791  1/1982  Bernstein ........................ 435/26

Primary Examiner—Esther M. Kepplinger
Attorney, Agent, or Firm—Dale R. Lovercheck; Charles L. Lovercheck; Wayne L. Lovercheck

[57] ABSTRACT

A method of detection of neoplastic tissue comprising, providing a first solution, the first solution comprising cytosol malate dehydrogenase from a mammalian test tissue, determining a first rate or a first function of the first rate at which the first solution catalyzes the reaction of oxaloacetate to malate, comparing the first rate or first function of the first rate with a known standard normal rate or function of the normal rate at which a normal solution of cytosol malate dehydrogenase catalzes the reaction of oxaloacetate to malate, whereby the first rate or the first function of the first rate being substantially higher than the known standard normal rate or function of the normal rate indicated that the mammalian test tissue is neoplastic.

6 Claims, 4 Drawing Figures

MALATE DEHYDROGENASE METHOD

REFERENCE TO PRIOR PATENTS AND APPLICATIONS

This case is a continuation in part of patent application Ser. No. 431,028 filed Sept. 30, 1982, now U.S. Pat. No. 4,543,327 which was a continuation in part of application Ser. No. 340,132 filed Jan. 18, 1982, now abandoned, which was a continuation of application Ser. No. 158,121, filed June 10, 1980 now issued as U.S. Pat. No. 4,311,791.

REFERENCE OF PRIOR ART

U.S. Pat. No. 3,862,010 issued Jan. 21, 1975.
U.S. Pat. No. 4,003,795 issued Jan. 18, 1977.
Publication cited in U.S. Pat. No. 4,311,791.

The method disclosed herein is applicable to automated instruments which is a heretofore unanswered need in the art as noted by the Wilkinson reference cited in U.S. Pat. No. 4,003,795. This need is answered by the elimination of the preincubation step required in previous methods.

INTRODUCTION

Malate dehydrogenase (MDH, EC 1.1.137) catalyzes the reversible reduction of oxaloacetate to malate in the presence of NADH. Its existence as separate isoenzymes in the cytosol and in the mitochondria is associated with the function of a shuttle system (the malate-aspartate shuttle) for the transport of reducing equivalents from the cytosol into the mitochondria. Investigations of whether or not the enzymes in the malate-aspartate shuttle of tumor tissues are structurally and functionally identical to those of normal tissues have identified an aberrant cytoplasmic malate dehydrogenase in human tissues (Table 1) and serum of patients (Table 2) with malignant neoplasms as well as in Novikoff hepatoma cells, Morris minimal deviation hepatoma (H5123) and ethionine-induced hepatoma. Whereas the $K_m$ for oxaloacetate of the cytoplasmic MDH from normal human liver extracts is 40 uM, the $K_m$ value of the aberrant enzyme is characteristically about 1 mM.

GENERAL STATEMENT OF INVENTION

The determination of increased LD-5 activity may reflect the breakdown of tissue having high rates of glycolysis. It is carried out routinely on the serum, the pleural fluid or the ascitic fluid of patients with metastatic or primary neoplasm in the thorax or abdomen. The appearance of an increased LD activity in pleural fluid or ascitic fluid requires the measurement of inhibition of LD by pyruvate to determine the subunit content of LD. The presence of increased LD activity in pleural fluid or ascitic fluid also requires the measurement MD activity for the aberrant isoenzyme. The aberrant MD activity is thought to be related to the mechanism of increased glycolysis with increased LD-5 activity.

GENERAL DESCRIPTION OF DRAWINGS

FIG. 1 is a Lineweaver-Burk plot of the cytoplasmic malate dehydrogenase activity from rat liver as a function of oxaloacetate concentration. Assay mixtures contained 0.14 mM NADH, the indicated amount of oxaloacetate and an appropriate amount of the enzyme in 0.1M phosphate buffer, pH 7.0. Total volume 3 ml.

DETAILED DESCRIPTION OF THE INVENTION

Figure 1:
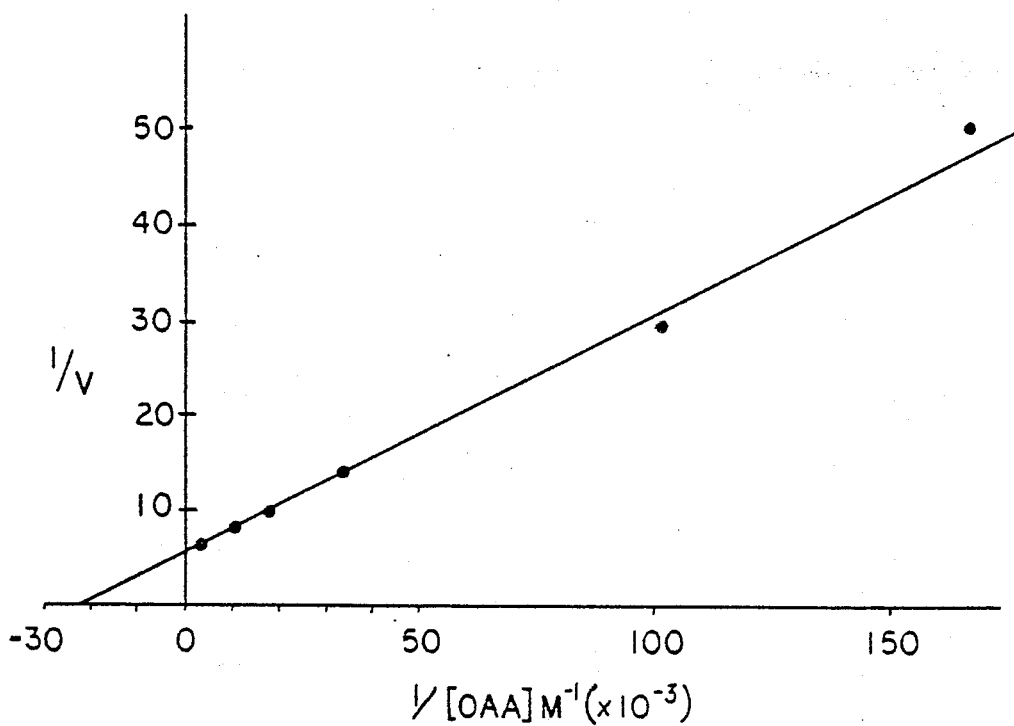
Figure 2:
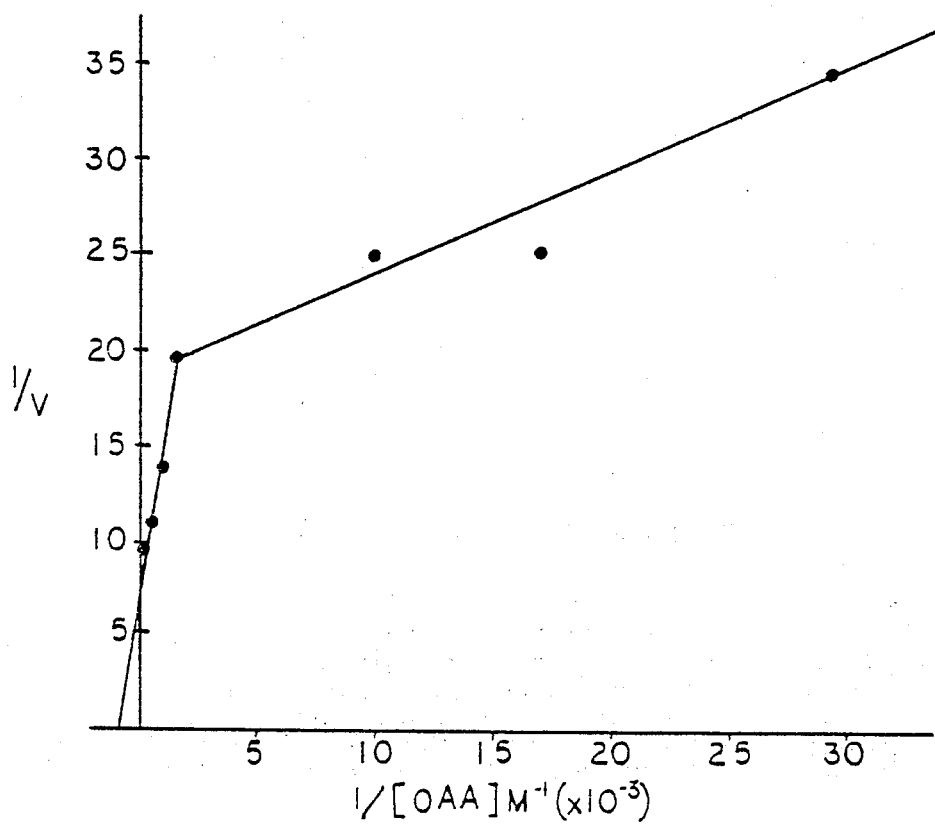
FIG. 2 is a plot similar to FIG. 1 using rat Novikoff hepatoma tissue.
Figure 3:
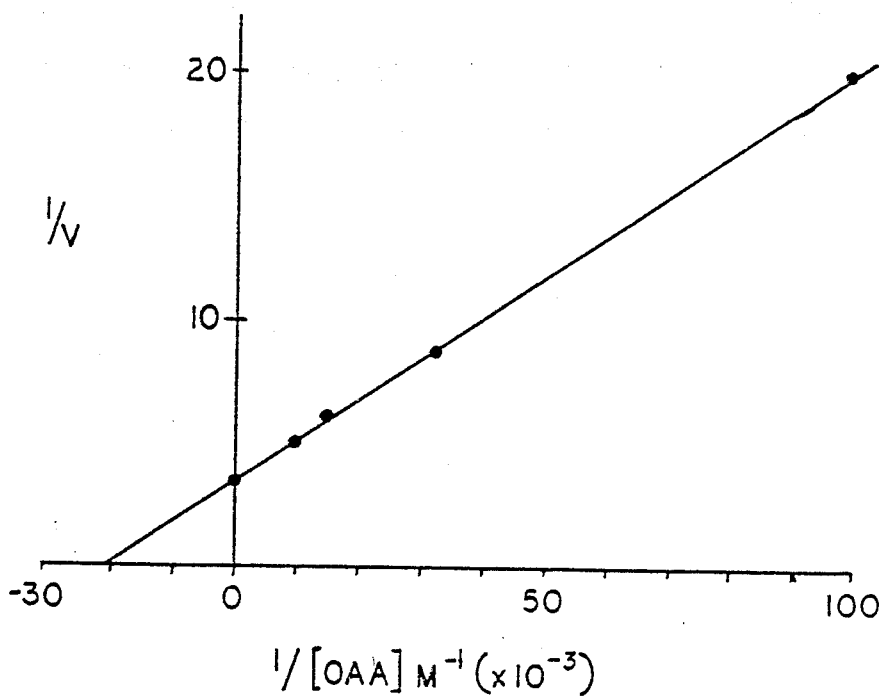
FIG. 3 is a Lineweaver-Burk plot of the cytoplasmic malate dehydrogenase activity from human liver as a function of oxaloacetate concentration. Assay mixtures were as described in the legend of FIG. 1.
Figure 4:
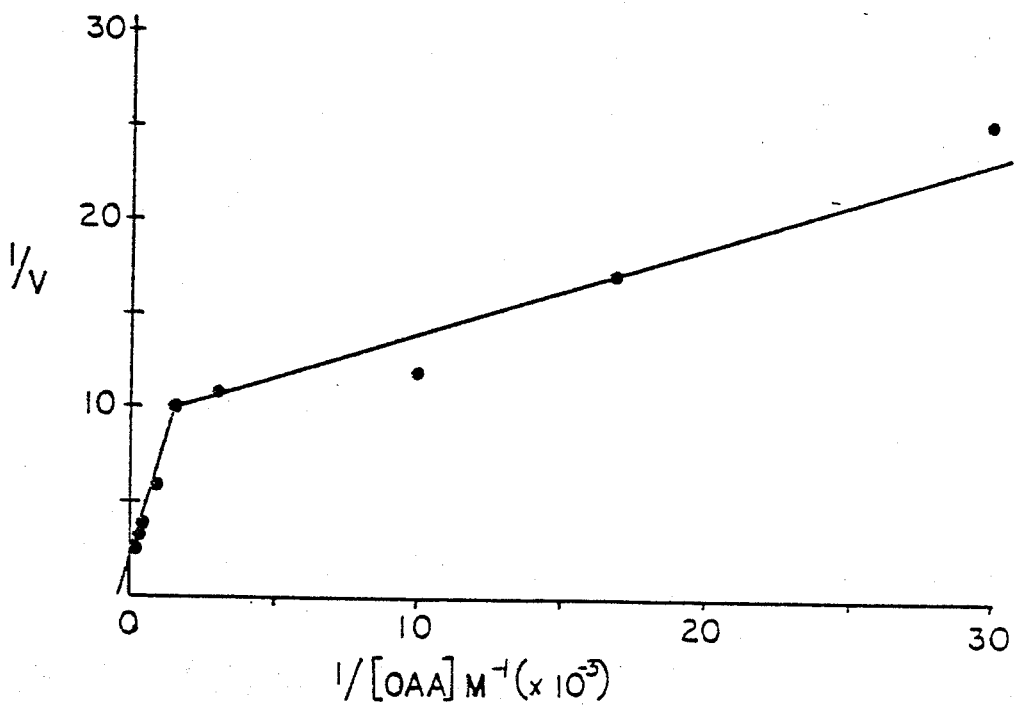
FIG. 4 is a plot similar to FIG. 3 using human adenocarcinoma tissue.

Malate dehydrogenase (MDH, EC 1.1.1.37) catalyzes the reversible reduction of oxaloacetate to malate in the presence of NADH. In eukaryotic cells the enzyme is generally found to be present as two distinct isoenzymes; one form is present in the cellular cytosol and the other is present exclusively in the mitochondria. These two isoenzymes form part of a shuttle system (the malate-aspartate shuttle) that functions as the major mechanism for the transportation of reducing equivalents from the cytosol into the mitochondria.

As part of the ongoing studies on the mechanism of action and metabolic function of the malate dehydrogenases (1–3) we recently investigated the kinetic properties of the two isoenzymes present in rat Novikoff hepatoma tissues. These studies were initiated to evaluate whether or not the enzymes in the malate-aspartate shuttle of tumor tissues are structurally and functionally identical to those of normal tissues.

The inhibition of LD activity by pyruvate is described in the procedure requiring the comparative assay at 5 mM and 0.34 mM pyruvate. Inhibition of LD activity of less than 35% is indicative of predominantly LD-5 isoenzyme activity.

The unusual cytoplamic MD can be demonstrated by performing two assays: one at an oxaloacetate concentration of 0.33 mM and the other at an oxaloacetate concentration of 6.6 mM. Both substrate concentrations are well above the Km of the normal cytoplasmic MD and the rate of NADH oxidation should be independent of the oxaloacetate concentration. Therefore, the ratio of the two rates should be close to unity. When such assays were done on the sera of about 20 healthy individuals values between 0.8 and 1.0 were obtained for the two assays. The ratios were between 2.0 and 3.0 in assays of sera from patients with malignant neoplasm (Table 2) indicating the presence of an enzyme with a high Km value for oxaloacetate.

The analysis of serum samples for MD activity combined with the analysis of LD-5 activity appears to be a potentially useful tool in the diagnosis of malignancy.

EXAMPLES

Fresh tumor or liver tissue was homogenized with a glass tissue homogenizer in 0.1M potassium phosphate buffer, pH 7.5, containing 0.25M sucrose. The homogenate was centrifuged for 10 min at 10,000 xg to remove tissue debris. The supernatant was then centrifuged for 30 min at 20,000 xg to obtain a high-speed supernatant that contains the cytoplasmic enzymes. The supernatant did not contain any isocitrate dehydrogenase activity or transhydrogenase activity and was therefore judged to be free of mitochondrial enzymes. This high-speed supernatant was used without further fractionation for the experiments described below.

A determination of the $K_M$ values for the cytoplasmic enzyme yielded the values listed in Table 1. The $K_M$ values of the mitochondrial enzyme from the hepatoma tissue are identical with the values obtained with the enzyme from normal liver mitochondria. The cytoplasmic enzymes also have identical $K_M$ values for the coenzyme; however, the Lineweaver-Burk plots for the substrates were non-identical. Whereas the $K_M$ value for oxaloacetate obtained with the liver enzyme is approximately 55 mM, the Lineweaver-Burk plot obtained with the hepatoma enzyme displayed two slopes. One of the slopes corresponded with a $K_M$ value that is approximately identical to that of the liver enzyme, whereas the other slope yielded a $K_M$ value for oxaloacetate of about 1 mM. A similar phenomenon was observed when malate was used as the substrate; however, the difference between the two slopes was less extensive than with oxaloacetate.

TABLE 1

Km FOR OXALOACETATE IN TISSUE HOMOGENATES OF HUMAN ORIGIN

| Tissue | Km (mM) |
|---|---|
| Adenocarcinoma of breast | 1.0, 1.2 |
| Adenocarcinoma of colon | 1.0 |
| Adenocarcinoma of uterus | 1.0 |
| Lymphocytic leukemia | 1.1 |
| Squamous cell carcinoma of larynx | 0.9 |
| Normal liver | 0.04 |

TABLE 2

SERUM FROM PATIENTS WITH CANCER

| Neoplasm | Km | Ratio* |
|---|---|---|
| Lymphocytic leukemia | 0.90 | 2.0 |
| Adenocarcinoma, metastatic, liver | 1.1 | 2.1 |
| Adenocarcinoma, colon | 1.0 | 2.1 |
| Adenocarcinoma, ovary | 1.0 | 2.0 |
| Normal | 0.05 | 1.0 |

*Ratio = Reaction velocity at 6.8 mM OAA divided by velocity at 0.34 mM OAA

Novikoff hepatoma tissue contains two cytoplasmic enzymes that possess MD activity, one of which closely resembles that present in the rat liver cytoplasm. The other enzyme, having a $K_M$ of about 1 mM, is not found in normal liver tissue.

In order to determine whether the normal cytoplasmic MD activity in the hepatoma tissue was due to a contamination of the tumor tissue with normal tissue, we purified the Novikoff hepatoma cells by growing them in tissue culture using a Dulbecco's modified essential medium, and transferring the culture until only neoplastic cells could be detected in the culture. An extract of these cells was subsequently used for the determination of the cytoplasmic MD activity. It appears thus that hepatoma cells contain the aberrant cytoplasmic MD in addition to the normal enzymes.

An extensive search for the presence of the aberrant enzyme in any normal rat tissue yielded negative results. The presence of the unusual enzyme was detected, however, in extracts of fetal rat liver. The data obtained thus far suggest that the enzyme with the low affinity for oxaloacetate is present during the early fetal stages, but gradually disappears during the gestation period. None of the aberrant enzyme appears to be present in the livers of newborn rats.

The same differences in catalytic properties were found when the MD of Sprague Dawley and Buffalo livers were compared with the hepatoma H5123 (Morris minimal deviation) and hepatoma 19 (ethionine-induced rapidly growing tumor) and the uninvolved liver controls from the same animals. In these experiments, typically, oxaloacetate saturation was not achieved below 3.5–7 mmol/l for maximum MD activity of the tumor. These changes were also observed in the virus induced leukemia of the hamster.

A cytoplasmic MD with characteristics similar to those of the aberrant MD is also present in various human tumors. The various types of neoplasia thus far investigated that contain the unusual MD are listed in Table 2. The unusual enzyme was absent in extracts of a granuloma and a fibroma. The latter tissues yielded double reciprocal plots with a single slope that closely resembles that obtained with extracts from normal liver tissues. The $K_M$ for oxaloacetate of the cytoplasmic MD from normal human liver extracts was found to be 40 mM. Double reciprocal plots of the data obtained from all other tissues listed in Table 1 yielded two slopes. The $K_M$ value of the aberrant enzyme is again about 1 mM.

The unusual cytoplasmic MD can also be detected in the serum of animals and patients with neoplastic disease. To demonstrate this two assays were done; one at an oxaloacetate concentration of 0.33 mM and the other at an oxaloacetate concentration of 6.6 mM. Both substrate concentrations are well above the $K_M$ of the normal cytoplasmic MD and the rate of NADH oxidation should be about independent of the oxaloacetate concentration. Therefore the ratio of the two rates should be close to unity. When such assays were done on the sera of about 20 healthy individuals values between 0.8 and 1.0 were obtained for the ratios of the two assays. Using sera obtained from patients with neoplastic disease we obtained ratios between 2.0 and 3.0, indicating the presence of an enzyme with a high $K_M$ value for oxaloacetate.

An analysis of serum samples for MD activity as described here could be a useful tool in the early diagnosis of certain malignant growths. In addition, the technique could be used to evaluate the effectiveness of various therapeutic treatments as well as of the surgical removal of a malignancy.

Two possibilities deserve consideration. The first possibility is that the activity represents a hitherto unknown MD isoenzyme that is only present during embryonic development and in certain neoplasms. It is very difficult to see, however, how the presence of a MD isoenzyme with a very high $K_M$ for oxaloacetate can provide a metabolic advantage to rapidly growing cells. If this is the case then the non-specific dehydrogenase must be present in much higher concentrations in tumor tissues than in normal tissues, since we could not detect the enzyme in normal tissue extracts. Lactate dehydrogenase would be a likely candidate since it is closely related to MD in many respects. We therefore assayed several tumor extracts as well as normal tissue extracts for lactate dehydrogenase activity. Although we found a somewhat increased level of lactate dehydrogenase in the tumor tissue extracts, the differences could not possibly explain the aberrant MD activity present in the tumors.

In a preferred embodiment of the invention a method is provided of detection of neoplastic tissue including providing a solution including cytosol malate dehydrogenase from a mammalian test tissue, determining the rate at which this solution catalyzes the reaction of oxaloacetate to malate, and then comparing the rate with a known standard normal rate at which a normal solution of cytosol malate dehydrogenase catalyzes the reaction of oxaloacetate to malate, so that a rate substantially higher than the known standard normal rate is an indication that the animal test tissue is neoplastic.

In another embodiment of the invention a method is provided of detection of neoplastic tissue including providing a first solution including oxaloacetate and NADH, providing a second solution having a substantially higher concentration of oxaloacetate and NADH, adding a portion of cytoplasmic malate dehydrogenase from a test solution to the first solution to form a first malate dehydrogenase solution, adding a portion of cytoplasmic malate dehydrogenase from the test solution to the second solution to form a second malate dehydrogenase solution. The concentration of malate dehydrogenase in the first solution is about equal to the concentration of malate dehydrogenase in the second solution. The rate of NADH reaction with oxaloacetate is then determined in the first malate dehydrogenase solution to obtain a first malate dehydrogenase reaction rate. The rate of NADH reaction with oxaloacetate is then determined in the second malate dehydrogenase solution to obtain a second malate dehydrogenase reaction rate. The first malate dehydrogenase reaction rate is then compared with the second malate dehydrogenase reaction rate, whereby a substantially higher second malate dehydrogenase reaction rate as compared to the first malate dehydrogenase reaction rate indicates that the test tissue is neoplastic. The first malate dehydrogenase reaction rate may be compared with the second malate dehydrogenase reaction rate as a ratio wherein the first malate dehydrogenase reaction rate used as the denominator and the second malate dehydrogenase reaction rate is used as the numerator. Preferably, a ratio of 2.0 or more denotes a detection of neoplastic tissue.

The determination of the rate of NADH reaction with oxaloacetate in the first and second oxaloacetate solutions of malate dehydrogenase, preferably includes adding pyruvate and lactate dehydrogenase to the product solutions of the first and to the second oxaloacetate solutions of malate dehydrogenase.

Alternatively, the malate dehydrogenase reaction rates are compared by comparing the Km of oxaloacetate or the reciprocal of the Km of oxaloacetate for the first and second oxaloacetate solutions.

The embodiments of the invention in which an exclusive property or privilege is claimed are defined as follows:

1. A method of diagnosing the presence of neoplastic cells in a malignant growth comprising:
   (a) providing a fluid from said malignant growth, said fluid containing cytoplasmic malate dehydrogenase,
   (b) determining whether said fluid comprises aberrant malate dehydrogenase,
   said determining comprising a reaction using said cytoplasmic malate dehydrogenase whereby the presence of aberrant malate dehydrogenase indicates the presence of neoplastic cells in said malignant growth.

2. The method recited in claim 1 wherein said determining further comprises the use of oxaloacetate.

3. The method recited in claim 1 wherein said determining further comprises the use of NADH.

4. A method of diagnosing the presence of neoplastic cells in a malignant growth comprising:
   (a) providing a fluid from said malignant growth, said fluid containing cytoplasmic malate dehydrogenase,
   (b) determining whether said fluid comprises aberrant malate dehydrogenase,
   said determining comprising reacting oxaloacetate using said cytoplasmic malate dehydrogenase whereby the presence of aberrant malate dehydrogenase indicates the presence of neoplastic cells in said malignant growth.

5. The method recited in claim 4 wherein said determining further comprises determining the rate of NADH oxidation in said fluid at two oxaloacetate concentrations,
   both of said oxaloacetate concentrations being substantially above the Km of normal cytoplasmic malate dehydrogenase.

6. A method of indicating the presence of neoplastic cells in a patient comprising:
   (a) providing a fluid from said patient, said fluid containing cytoplasmic malate dehydrogenase,
   (b) determining whether said fluid comprises aberrant malate dehydrogenase by determining the rate of NADH oxidation in said fluid at two substrate concentrations,
   both of said substrate concentrations being substantially above the Km of normal cytoplasmic malate dehydrogenase whereby the presence of aberrant malate dehydrogenase indicates the presence of neoplastic cells in said patient.

* * * * *